United States Patent [19]

Oftedahl et al.

[11] 4,397,995

[45] Aug. 9, 1983

[54] POLYMERIC ANTI-TUMOR AGENT AND METHOD OF PREPARATION

[75] Inventors: Marvin L. Oftedahl, Warson Woods; Howard M. Solomon, Ballwin, both of Mo.; James A. Webster, Dayton, Ohio

[73] Assignee: Monsanto Company, St. Louis, Mo.

[21] Appl. No.: 221,087

[22] Filed: Dec. 29, 1980

[51] Int. Cl.$^3$ .................... C08F 222/40; C08F 8/30; A61K 31/74

[52] U.S. Cl. .................... 525/374; 524/378; 525/327.4

[58] Field of Search .............. 525/328, 374; 524/378

[56] References Cited

U.S. PATENT DOCUMENTS

| | | | |
|---|---|---|---|
| 2,854,357 | 1/1958 | Johnson et al. | 117/138.8 |
| 2,883,287 | 4/1959 | Fields et al. | 99/154 |
| 2,892,736 | 6/1959 | Johnson et al. | 117/138.8 |
| 2,930,775 | 3/1960 | Fordyce et al. | 260/29.6 |
| 2,957,767 | 10/1960 | Williams | 96/114 |
| 3,157,595 | 11/1964 | Johnson et al. | 210/54 |
| 3,261,798 | 7/1966 | Farley | 260/29.6 |
| 3,282,879 | 11/1966 | Werner, Jr. | 260/29.6 |
| 3,651,171 | 3/1972 | von Bonin et al. | 525/328 |
| 3,840,499 | 10/1974 | Di Giulio | 260/78.5 T |
| 4,255,537 | 3/1981 | Fields et al. | 525/328 |

FOREIGN PATENT DOCUMENTS 664326  6/1963  Canada .

OTHER PUBLICATIONS

U.S. Patent application Ser. No. 5,638 to Joseph E. Fields et al., filed Jan. 22, 1979.

*Primary Examiner*—Joseph L. Schofer
*Assistant Examiner*—Peter F. Kulkosky
*Attorney, Agent, or Firm*—Scott J. Meyer; James W. Williams, Jr.

[57] ABSTRACT

An improved pharmaceutically active derivative of a copolymer of olefin monomer and $\alpha,\beta$-unsaturated polycarboxylic anhydride is prepared by reacting the copolymer with aqueous ammonia, spray drying the resulting aqueous solution of half-amide, half-ammonium salt and thermally imidating the resulting substantially dry, solid particulate product by simultaneous treatment with elevated temperature and removal of water until 5–40% of the derivative half-amide, half-ammonium salt groups are converted to imide groups.

7 Claims, No Drawings

POLYMERIC ANTI-TUMOR AGENT AND METHOD OF PREPARATION

BACKGROUND OF THE INVENTION

This invention relates to polymeric compounds useful as antitumor agents.

Various naturally-occurring and synthetic polyanionic materials have been investigated heretofore for their antitumor and related pharmaceutically active properties. One class of the synthetic polymers which has received considerable attention and study over the years is the class of polycarboxylates derived from ethylene/maleic anhydride (EMA) copolymers. The antitumor properties of these polymeric compounds were described at an early date by Regelson et al., *Nature* (London) 186, 778–80 (1960) and in Canadian Pat. No. 664,326, corresponding to U.S. Application Ser. No. 758,023, filed Oct. 28, 1958, now abandoned. According to the latter patent, the useful molecular weight of these polymers is said to range between 500 and 1.5 million. One of these polymers, the half-amide, half-ammonium salt of EMA having an average molecular weight of 20,000–30,000 was later reported to be chronically toxic in rodents and dogs. Mihich et al., *Fed. Proc.* Vol. 19, No. 1, Pt. 1, p. 142a, March 1960. Chronic toxicity also was later reported with the 2000–3000 molecular weight polymer in dogs by Mihich et al., *Fed. Proc.* Vol. 20, No. 1, Pt. 1, p. 407a, March 1961. These findings of toxicity militated against clinical testing of the polymers.

More recently, certain new derivatives of the EMA type copolymers having a relatively low average molecular weight of from about 300 to about 1500 were found to have far less toxicity than the higher molecular weight copolymers and to have more useful antitumor properties. These copolymers were derivatized to contain both a half-amide, half-carboxylate salt function and an imide function in which the latter function comprised from about 5% to about 40% by weight of the two functions. Further description of these derivatized copolymers can be had by reference to copending application Ser. No. 5638, filed Jan. 22, 1979, and assigned to a common assignee.

As described in said copending application Ser. No. 5638, the latter copolymers are preferably derivatized by ammoniation in organic solvents in a two-stage process. In the first stage, the EMA type copolymer is reacted with liquid ammonia in acetone to prepare the intermediate half-amide, half-ammmonium salt (AEMA). The AEMA precipitates out of solution and is recovered by filtration, centrifugation and the like separation procedures. The imide-containing derivative is then prepared in a second stage by reacting the intermediate AEMA with ammonia in a suitable solvent such as xylene or toluene at refluxing temperatures while concurrently removing water until the desired percentage of imide is formed.

It has been found subsequently that the aforesaid derivatization in organic solvents gives rise to undesirable by-product contaminants in the final product which are now desired to be avoided for pharmaceutical use of the product. These contaminants cause an undesirable darkening of the final product. Although the specific composition of the by-product contaminants has not been identified, it is known, for example, that aldol condensation can occur with acetone in basic media (as can be provided by ammonia) to yield compounds such as diacetone alcohol, mesityl oxide, phorone, isophorone and diacetone amine. See, for example, Fieser and Fieser, "Advanced Organic Chemistry", pp. 457–8, Reinhold Publishing Corporation, New York, 1961, and Royals, "Advanced Organic Chemistry", pp. 759–61, Prentice-Hall, Inc., New York, 1961. The present invention is directed to overcoming the problem of these and other such contaminants.

Elimination of organic solvents in the method of producing the copolymer derivatives is further desired to improve filterability during processing and to avoid the possibility of fire hazards with flammable materials.

DESCRIPTION OF THE INVENTION

In accordance with the present invention, low molecular weight copolymers of the general type described hereinbefore which are derivatized to contain both a half-amide, half-carboxylate salt function and an imide function are significantly and substantially improved by ammoniation in aqueous phase and by thermal imidation to form the derivatized copolymer in the absence of organic solvent media.

The starting copolymers for use in the invention are copolymers of at least one olefin monomer having from 2 to about 4 carbon atoms and at least one $\alpha,\beta$-unsaturated polycarboxylic anhydride having from 4 to about 6 carbon atoms, and an average molecular weight of from about 300 to about 1500. These copolymers are derivatized to contain both (a) half-amide, half-carboxylate salt groups and (b) imide groups in which said imide groups comprise from about 5% to about 40% by weight of said derivatized groups.

Illustrative examples of the foregoing olefin monomers are ethylene, propylene and isobutylene; illustrative examples of the foregoing polycarboxylic anhydrides are maleic anhydride, citraconic anhydride and aconitic anhydride. Of these monomeric components, ethylene and maleic anhydride are preferred. Illustrative examples of the copolymers are copolymers of propylene and maleic anhydride, copolymers of ethylene and citraconic anhydride and the preferred copolymers of ethylene and maleic anhydride.

In the final derivatized copolymer product, the imide groups preferably comprise from about 10% to about 25% by weight of the derivatized groups (a) and (b).

A small portion (believed to be less than 10%) of monoammonium carboxyl or other pharmaceutically acceptable salt groups and/or dicarboxyl group also can be present as may derive from partially reacted or unreacted anhydride during the preparation of these polymeric compounds.

Although the final derivatized product also can be converted to pharmaceutically acceptable salt derivatives other than ammonium, for example, sodium and potassium, ammonium is preferred.

The imide groups also can be N-alkylated with alkyl groups having from one to four carbon atoms but remain unsubstituted in the preferred product described hereinafter.

A particularly desirable example of the final derivatized copolymer product is prepared from a base copolymer of ethylene and maleic anhydride having an average molecular weight of about 850 and derivatized to contain both (a) half-amide, half-ammonium salt groups and (b) imide groups in which the imide groups comprise about 18% by weight of said derivatized groups.

The stated molecular weight of about 850 for the foregoing illustrative base copolymer of EMA is the number average molecular weight ($M_n$) as determined by Vapor Pressure Osmometry in dry DMF at 120° C. using a Knauer VP Osmometer. This copolymer product also has a specific viscosity (1% in DMF at 25° C.) of about 0.06 when measured by capillary viscometry using a Cannon Ubblehode dilution size 75 auto-timed viscometer. These are conventional methods for the determination of molecular weight of polymeric materials and correspond to methods disclosed in copending application Ser. No. 5638 for EMA type copolymers.

In two alternative methods, molecular weight of the corresponding partially imidated (18% imide) derivative of AEMA was calculated by carbon-13 NMR spectroscopy as about 1339 and by proton NMR spectroscopy as about 1460.

For convenience hereinafter, the stated molecular weight of the EMA type copolymers shall mean number average molecular weight as determined by Vapor Pressure Osmometry in dry DMF at 120° C.

In accordance with a preferred method of the invention, the starting copolymer is reacted with aqueous ammonia ($NH_4OH$) to form an aqueous solution of the half-amide, half-ammonium salt which is then spray dried to form a substantially dry, solid particulate form of the intermediate product. The spray dried intermediate product is then thermally imidated by simultaneous treatment with elevated temperature and removal of water until the desired percentage of imide is formed. Imide content can be determined by conventional infrared spectrometry as described in the above-mentioned copending application Ser. No. 5638.

The initial reaction of the starting copolymer, e.g. EMA, with aqueous ammonia is preferably carried out by reacting solid EMA with concentrated $NH_4OH$ (e.g. about 7.5–15 N) at ambient temperature (about 10°–25° C.). Dilute ammonium hydroxide also can be used as long as at least two equivalents (or moles) of $NH_3$ (or $NH_4OH$) are used per equivalent (or mole) of anhydride in the base copolymer. However, the use of dilute ammonium hydroxide may require the removal of more water than otherwise necessary to provide a substantially dry product in the subsequent spray drying step. The reaction product can be filtered to provide a clear and virtually colorless solution of the half-amide, half-ammonium salt of EMA (ammoniated EMA or AEMA). It should be understood that the terms EMA and AEMA are used herein for convenience in illustrating the method of the invention and that other copolymers and ammoniated copolymers as defined hereinbefore are included within the scope of the disclosed invention.

In some instances, depending upon the purity and condition of the starting EMA copolymer, certain volatile organic contaminants may be occluded in the AEMA solution. For example, in the preparation of the base EMA copolymer, the monomer components are generally reacted in the presence of organic solvents such as benzene, halobenzenes, haloparaffins and alkylated aromatic hydrocarbons such as ethyl benzene as described in U.S. Pat. Nos. 2,857,365; 2,913,437; 2,938,016; and 2,980,653. Even trace amounts of volatile organic residues carried over into the AEMA from the starting EMA copolymerization are preferably removed from the AEMA solution. It has been found that vacuum distillation or "topping" of the aqueous EMA solution to remove a small amount of distillate (about 1–2% by volume) provides a product free from detectable volatile organics (non-detectable by conventional liquid or gas chromatographic analytical procedures). Heating at a temperature of from about 20° C. to about 80° C. and preferably at about 60° C., at reduced pressure of from about 10 to about 28 and preferably about 25 inches Hg., for about 30 to about 360 minutes and preferably about sixty minutes, effectively removes these residual volatile organics.

Spray drying of the aqueous solution of half-amide, half-ammonium salt can be carried out in conventional spray drying equipment for the aseptic and sanitary processing of pharmaceuticals and biochemicals. The spray drying is preferably carried out by prefiltering the aqueous solution through a submicron filter and then spraying through an atomizing nozzle into a spray drying chamber having an inlet temperature of from about 150° C. to about 300° C. and an outlet temperature of from about 70° C. to about 150° C. The inlet and outlet temperatures preferably are, respectively, about 200° C. and 100° C. The resulting spray dried product is a fine white powder having a moisture content of less than about 12% and a whiteness corresponding to an APHA color (2% solution in water) not in excess of about 60 and preferably not in excess of about 20.

In some cases, the spray drying may cause the formation of undesirable peroxide contaminants. This peroxide formation can be avoided by incorporating a small but effective amount of a water soluble bisulfite salt, preferably metabisulfite salt, into the aqueous solution prior to spray drying. Illustrative examples of useful water soluble bisulfite salts are the alkali metal bisulfites and metasulfites, e.g., sodium and potassium, and the ammonium acid sulfite. $Na_2S_2O_5$ is the preferred water soluble bisulfite salt. An amount of these substances of from about 0.05% to about 0.2% by weight is suitable for purposes of avoiding peroxide formation. Use of higher amounts preferably is avoided in order to meet U.S. Pharmacopoeia standards for use in parenteral products.

Thermal imidation of the spray dried intermediate half-amide, half-ammonium salt (e.g., AEMA) can be carried out by subjecting the solid material to an elevated temperature, preferably from about 60° C. to about 150° C., while preferably removing water of the reaction such as by use of a nitrogen or other inert gas sweep or vacuum. It is important to monitor the thermal imidation reaction carefully to ensure production of a final product having an imide content of from about 5% to about 40% by weight as determined by infrared spectrometry.

Other pharmaceutically acceptable cationic salt forms of the derivatized copolymer can be prepared by conventional ion exchange techniques. For example, conversion to the sodium and potassium salt forms can be carried out by ion exchange of the ammonium salt with Rohm & Haas IRC-120 resin, and similar such ion exchange resins, in the sodium and potassium ion forms, respectively.

The derivatized copolymeric product as prepared above can be placed into any suitable dosage form. Thus, the bulk drug product can be reconstituted by dissolving in pyrogen-free water, adjusted to pH of about 9.5, sterile filtered, filled into unit dosage vials of desired capacity and then lyophilized or freeze dried. Alternatively, the reconstituted aqueous product can be sterile filtered, aseptically spray dried and directly filled into unit dosage vials.

The derivatized copolymeric product can be administered to a warm-blooded animal by a variety of conventional routes, especially intravenously and intraperitoneally. Such administration preferably is in aqueous solution such as in sterile water or physiologically normal saline (0.9% NaCl) and can be carried out by suitable reconstitution of the above-prepared lyophilized, freeze dried or spray dried solid materials. The derivatized copolymeric product also can be administered orally in the form of tablets, powders, capsules, elixers and the like dosage forms and can be used in admixture with common solid and liquid fillers, diluents, carriers, suspending agents and adjuvants such as, for example, cornstarch, lactose, talc, stearic acid, magnesium stearate, carboxymethyl cellulose, gelatin, acacia and locust bean gums, alcohol, water, dimethylsulfoxide, vegetable oils and the like materials. The liquid oral dosage form also preferably is solid reconstituted in liquid mixture at the time of administration in order to maintain stability of the dual groupings of (a) half-amide, half-carboxylate salt and (b) imide.

The dosages for administration of the polymeric compounds reported in copending application Ser. No. 5638, filed January 22, 1979, were exemplified at from about one to about 100 mg/Kg of body weight to provide an immune response and related antitumor activity against certain animal tumors. It has been found subsequently that antitumor activity against certain other animal tumors is enhanced at a substantially higher, non-toxic dose level of 300 to 2000 mg/Kg of body weight. Accordingly, the improved polymeric compounds prepared by the method of the present invention preferably can be administered at dosages ranging from about one to about 2000 mg/Kg of body weight. Illustrative polymeric products prepared from EMA copolymer (Mol. wt$\approx$850) and derivatized to contain about 14–22 wt% imide have relatively low acute toxicity in mice and rats with an $LD_{50}$ approximating 2.5 g/Kg when administered intraperitoneally and 1.5–1.75 g/Kg when administered intravenously.

The method of preparing the derivatized copolymer product in accordance with this invention provides several advantages over the prior methods of preparation. The presence of undesirable occluded organic solvents is avoided, a product of greater whiteness is obtained by eliminating the production of certain by-product contaminants, and a polishing filtration can be carried out more readily since the product is reconstituted in aqueous solution instead of suspension in organic solvent media during the various processing steps. In a representative example, an aqueous ammoniated, thermally imidated EMA copolymer derivative made according to this invention exhibited an APHA color (2% solution in water) of 15 and contained no detectable toluene or xylene volatile residue whereas similar EMA copolymer derivatives prepared by ammoniating in acetone solution and imidating by refluxing in a mixture of toluene and xylene exhibited an APHA color (2% solution in water) of 200 and contained 94 ppm toluene and 31 ppm xylene residue in one lot and 30 ppm toluene and 400 ppm xylene residue in another lot.

The improved product prepared in accordance with this invention exhibits significant activity in certain antitumor tests in standard laboratory experimental animals. Thus, in tests for activity against Lewis lung carcinoma implanted subcutaneously in $B6D2F_1$ mice, substantial improvement in inhibition of primary tumor growth was observed in animals treated with the product made in accordance with this invention when compared to untreated control animals. The Lewis lung carcinoma is generally recognized as a severely intractable tumor condition against which most antitumor compounds are ineffective.

The following examples will further illustrate the invention, although it should be understood that the invention is not limited to these specific examples.

EXAMPLE 1

Aqueous Ammoniation of EMA

Into a 4-necked, 500 ml flask equipped with a stirrer and thermometer was added 200 ml of concentrated (15 N) ammonium hydroxide. Then 20 grams of solid ethylene/maleic anhydride (EMA) copolymer having a specific viscosity of about 0.06 (1% in DMF, 25° C.) (mol. wt.$\approx$850) was added portionwise with stirring while maintaining the temperature below 20° C. Filtration of the half-amide, half-ammonium salt (AEMA) product through a glass filter resulted in a clear and substantially colorless product.

EXAMPLE 2

Vaccum distillation and spray drying of aqueous AEMA

Thirty seven gallons of aqueous AEMA solution prepared by aqueous ammoniation of EMA (specific viscosity 0.06) and having a 22% solids content was topped by heating from 35° C. to 60° C. at reduced pressure of 25 inches Hg and holding at 60° C. for one hour. After this treatment, no volatile organics were detectable in the product as determined by liquid chromatography employing conventional reverse phase techniques whereas about 0.1% of such volatiles were detected prior to the aforesaid vacuum topping. The topped solution was filtered through a submicron filter (0.2$\mu$ pore size) and AEMA was isolated as a fine white powder by feeding the filtrate at 4 gallons/hour to a small spray dryer equipped with a two fluid nozzle and operating at an inlet drying temperature of 200° C. and an outlet temperature of 100° C. The resulting powder had an APHA color of 10 as a 2% aqueous solution.

The APHA color determinations herein were made substantially in accordance with the "Standard Methods for the Examination of Water and Sewage", American Public Health Association, New York, 1936, pp. 12–14, 22. According to this procedure, the color of the sample solution is compared to that of a series of standards by visual observation down through the solution in a Nessler tube onto a uniform white background. The base color in the standards is that of platinum while cobalt is used to vary the hue. The base color is prepared by dissolving 1.245 grams of potassium chloroplatinate ($K_2PtCl_6$), containing 0.50 g of platinum, in a solution containing 100 ml of distilled water and 100 ml of concentrated hydrochloric acid (12 N HCl). The darkest color standard is prepared by dissolving one gram of crystallized cobaltous chloride ($CoCl_2.6H_2O$), containing 0.248 g of cobalt, in the platinum solution and diluting to one liter with distilled water. This solution is assigned an upper color number 500. Gradations of color from 0 to 500 are then made by appropriate dilutions of the latter solution in distilled water. For example, for 50 ml volumes of color standards, a standard with a color number of 10 is prepared by diluting a one ml aliquot of the number 500 standard to 50 ml while a standard with a color number of 100 is prepared by diluting a ten ml aliquot of the number 500 standard to 50 ml.

EXAMPLE 3

Spray drying of aqueous AEMA with Na₂S₂O₅

Another portion of the aqueous AEMA solution was spray dried in accordance with the procedure of Example 2 except that 0.2% of sodium metabisulfite ($Na_2S_2O_5$) was incorporated into the aqueous solution prior to spray drying. The resulting spray dried product was free from peroxide contaminants as determined by the standard starch/iodide test for peroxides. In accordance with this test, a starch solution in the presence of a trace of iodide is used to determine minute amounts of oxidizing agents, such as peroxide, capable of liberating iodine from an iodide to yield the characteristic blue color of a starch/iodide complex.

EXAMPLE 4

Partial imidation of spray dried AEMA

A small rotary double cone dryer was charged with 4700 g of AEMA (prepared substantially as in Example 3). The dryer was sealed and warmed over a nine hour period to 85° C. while under vacuum of <50 mm. The material was held for seven hours during this period at 85°–90° C. The dryer was then brought to atmospheric pressure with dry nitrogen. A 370 g quantity of condensate was collected during this period. Heating was continued at 90° C. with a nitrogen sweep for 20 hours. Infrared spectrometry of the dryer contents revealed that the polymeric powder contained 18% imide. The imidated product, a white powder (APHA color of 20 as a 2% aqueous solution), weighed 4000 g. This example also constitutes a step in Example 6 hereinafter.

EXAMPLE 5

Spray drying of aqueous solution of partially imidated AEMA

A 600 g amount of 50 wt% aqueous solution of thermally imidated AEMA (prepared substantially as in Example 4) was clarified by passage through a 0.4 micron filter. The final solid product was obtained as a fine white powder by spray drying the solution at 60 ml/min. feed rate in a small two fluid nozzle dryer operating at an inlet temperature of 175° C. and outlet temperature of 105° C. The powder had a 20% imide content (infrared) and a 2% aqueous solution had an APHA color of 20.

The final spray dried products of Examples 4 and 5 are readily mixed into aqueous solution without any significant dusting and without any detection of volatile organics, they form very clear solutions as the pH is raised to about 8.8 and are easily filtered through submicron filters in preparation for sterile filling into unit dosage vials.

EXAMPLE 6

Partially imidated AEMA for testing as a pharmaceutically active product was prepared and tested as follows:

Polymerization

Maleic anhydride (66 lb) was added to 510 lb of ethylbenzene in a stirred stainless steel reactor under nitrogen atmosphere. The mixture was stirred and warmed to 50° C. until solution was complete. To this solution was added a solution of 5.16 lb of benzoyl peroxide dissolved in 72 lb of ethylbenzene. The resulting mixture was transferred to a 100 gal reactor that had previously been cleaned, dried, purged with ethylene and prewarmed to 40° C. The reactor was then stirred and pressured to 60 psi with ethylene and warmed to 75° C. At 75° C. the pressure was increased to 200 psi. This was considered zero reaction time. A mild exotherm was observed, but was controlled within 2° C. of 75° C. by appropriate lowering of reactor jacket temperature. After three hours at 75° C. a second catalyst charge of 3.44 lb of benzoyl peroxide dissolved in 62 lb of ethylbenzene was pressured into the reactor through a transfer bomb. The temperature was held at 75° C. with the pressure at 200 psi for a total of 17 hours. The reactor was then cooled to 25° C., purged with nitrogen and the contents emptied into a filter. Collected solid was reslurried in 300 lb ethylbenzene and passed through an in-line slurry grinder onto a filter. The slurry ground solid was reslurried four times for one hour each time in 300 lb ethylbenzene, ground and filtered before transferring solids to a vacuum oven. Drying was carried out at 20 mm pressure, 60° C. with a slow nitrogen bleed into the vacuum oven until loss on drying analysis showed no further weight loss. The dry ethylene/maleic anhydride (EMA) copolymer product (62 lb) was collected and determined to have a specific viscosity of 0.055.

Ammoniation

A 100 gal reactor was charged with 188 lb of ammonium hydroxide (58%) and 91 lb of pyrogen free demineralized water. To this solution, EMA (as prepared above, 60 lb) was added in portions (approximately one lb/four minutes) at a temperature of 15°–25° C. Upon completion of EMA addition the mixture was stirred for a half hour at 30° C. whereupon solution was complete. The reaction mixture was then subjected to vacuum of 180–250 mm as the temperature was raised from 30° C. to 45°–50° C. over a period of 2 hours. Some foaming was evident but was not difficult to control. After one hour at 50° C. analysis by liquid chromatography showed no evidence of hydrocarbon impurities in the resulting AEMA solution. A solution of sodium metabisulfite (25 g) in 200 ml of water was then added, and the AEMA solution was filtered through 1 micron and 0.2 micron filters in series. The resulting pale yellow filtrate was refrigerated (5° C.) and retained for spray drying in the next step.

Spray Drying

Spray drying of the above filtered solution (22% solids) was carried out with a spray dryer inlet temperature of 195°–200° C. and an outlet of 70°–85° C. at rates of 7–8 lb/hr. Spray dried product in the amount of 19.1 Kg was collected for subsequent imidation.

The spray dried AEMA powder had a moisture content of 7.4%, a peroxide equivalent/gram of $4 \times 10^{-6}$, an APHA color of 10 as a 2% aqueous solution, and a particle size distribution of:

| | |
|---|---|
| <2.4μ | = 0.4% |
| 2.4–4.8μ | = 21% |
| 4.8–9.6μ | = 36% |
| 9.6–19.2μ | = 32% |
| >19.2μ | = 10% |

Oven Tray Static Imidation

Three vacuum ovens, each containing four trays were used for oven imidation. Ten trays were charged with portions of the above spray dried AEMA powder, 600–900 g each, for a total of 8300 g. Vacuum was applied for the first seven hours as the trays were equilibrating to the temperature range of 82°–90° C. From that point, the ovens were operated at atmospheric pressure with a slow stream of nitrogen. Samples were removed periodically for determination of imide/amide ratio by infrared spectroscopy, and trays were removed when the product approximated 17.5% imide. Imidated product was collected in the amount of 7.2 Kg. and assayed to have an APHA color of 10 as a 2% aqueous solution.

Imidation in Rotary Double Cone Dryer

A small rotary double cone dryer was charged with a 4700 g portion of the above spray dried AEMA powder. The dryer was sealed and warmed over 9 hours to 85° C. while under a vacuum of <50 mm. Vacuum was continued for an additional 7 hours at 90° C. The dryer was then brought to atmosphereic pressure with dry nitrogen. A 370 g quantity of condensate was collected. Heating was continued at 90° C. for an additional 20 hr with frequent monitoring of percent imide until infrared spectrometry indicated 18% imide. The partially imidated product (4000 g) was then collected in clean, double polyethylene bags as a white powder having an APHA color of 20 as a 2% aqueous solution.

Unit Dosage Processing

Product from the above oven tray static imidation and imidation in the rotary double cone dryer was blended together and retained as bulk drug for processing into unit dosage form as follows:

A 8754 g quantity of the bulk drug was processed into final dose form by dissolving in pyrogen free water and adjusting the pH to 9.5 with ammonium hydroxide. The resulting solution was sterilized by aseptic filtration and the sterile solution aseptically dispensed into aseptic sterile serum vials. The vials were aseptically lyophilized, capped, and packaged.

Pharmaceutical Testing

The thermally imidated product (18% imide) prepared by the foregoing method was tested at various dosages for its antitumor activity against Lewis lung carcinoma. In this test, $10^6$ Lewis lung cells were implanted s.c. in the right flank of male $B6D2F_1$ mice (10 per group). The test product was dissolved in sterile 0.9% NaCl solution and administered i.p. in a volume of 0.5 ml per mouse. Tumors were measured in perpendicular diameters on day 14 and tumor volume was calculated by the formula: length $\times$ width$^2 \times 0.5$. Mean and median tumor volumes were calculated for each treatment group and were compared with untreated controls to obtain a T/C ratio. The results are set forth in the following table:

| Dose (mg/kg. ip. $q^D$ 1–5) | Wt Change (gm) Day 7 | Wt Change (gm) Day 14 | Tumor Growth Inhibition (Day 14) N.P.$^a$ | Median Volume (mm$^3$) | T/C$^b$ | Mean Volume (mm$^3$) ± S.D. | T/C$^b$ |
|---|---|---|---|---|---|---|---|
| 2500 | −1.1 | +3.9 | 0/6 | 140 | .09 | 170 ± 97$^t$ | .11 |
| 1500 | +0.2 | +2.3 | 2/10 | 288 | .19 | 272 ± 211$^t$ | .18 |
| 900 | +1.0 | +2.0 | 2/10 | 304 | .20 | 372 ± 354$^t$ | .24 |
| 540 | +1.2 | +2.3 | 0/10 | 817 | .54 | 733 ± 369$^t$ | .48 |
| 324 | +1.0 | +2.3 | 1/10 | 1126 | .74 | 945 ± 449$^t$ | .61 |
| 194 | +1.3 | +1.5 | 1/10 | 804 | .53 | 737 ± 489$^t$ | .48 |
| 117 | +1.2 | +1.6 | 1/9 | 864 | .57 | 960 ± 571 | .62 |
| 70 | −2.3 | +2.1 | 1/10 | 426 | .28 | 486 ± 388$^t$ | .31 |
| Untreated Controls | +1.7 / +1.5 / +0.9 | +1.6 / +2.5 / +3.1 | 0/10 / 0/10 / 0/10 | 1369 / 2138 / 1132 } 1519 | | 1312 ± 815 / 1967 ± 923 / 1349 ± 629 } 1543 ± 829 | |

$^a$N.P. = mice without palpable tumors on day 14/total.
$^b$T/C = ratio of tumor volume in treated group relative to untreated controls.
$^t$Significantly different from untreated control at $p<.01$ by Student's t test.
$q^D$ = daily dosage, days 1 to 5.

Various other examples will be apparent to the person skilled in the art after reading the present disclosure without departing from the spirit and scope of the invention. It is intended that all such further examples be included in the scope of the appended claims.

What is claimed is:

1. The method of making an improved pharmaceutically active derivative of a copolymer of an olefin monomer having from 2 to about 4 carbon atoms and an α,β-unsaturated polycarboxylic anhydride having from 4 to about 6 carbon atoms, said copolymer having a number average molecular weight of from about 300 to about 1500, comprising reaction said copolymer with aqueous ammonia in an amount sufficient to form an aqueous solution of a copolymer derivative having half-amide, half-ammonium salt groups, spray drying said aqueous solution to provide a substantially dry particulate solid form of said copolymer derivative, and then thermally imidating said substantially dry copolymer derivative by simultaneous treatment with elevated temperature and removal of water until from about 5% to about 40% by weight of said derivative groups are converted to imide groups.

2. The method of claim 1 in which the aqueous solution of the half-amide, half-ammonium salt copolymer derivative is vacuum distilled to remove from about 1% to about 2% by volume of a distillate prior to said spray drying.

3. The method of claim 1 in which a small but effective amount of a water soluble bisulfite salt is incorporated in the aqueous solution of the half-amide, half-ammonium salt copolymer derivative prior to spray drying to prevent peroxide formation during said spray drying.

4. The method of claim 1 in which the copolymer is a copolymer of ethylene and maleic anhydride.

5. The method of claim 1 in which the imide groups comprise from about 10% to about 25% by weight of said derivatized groups.

6. The method of claim 1 in which the copolymer has an average molecular weight of about 850.

7. The method of claim 4 in which the imide groups comprise about 18% by weight of said derivatized groups and in which the copolymer has an average molecular weight of about 850.

* * * * *